(12) United States Patent
Fuchs

(10) Patent No.: US 9,919,306 B2
(45) Date of Patent: Mar. 20, 2018

(54) DOSING PIPETTE

(71) Applicant: STEVANATO GERMANY GMBH, Bad Oeynhausen (DE)

(72) Inventor: Karl-Heinz Fuchs, Radolfzell (DE)

(73) Assignee: Stevanato Germany GmbH, Bad Oeynhausen (DE)

( * ) Notice: Subject to any disclaimer, the term of this patent is extended or adjusted under 35 U.S.C. 154(b) by 0 days.

(21) Appl. No.: 14/653,393

(22) PCT Filed: Dec. 18, 2013

(86) PCT No.: PCT/EP2013/077210
§ 371 (c)(1),
(2) Date: Jun. 18, 2015

(87) PCT Pub. No.: WO2014/096081
PCT Pub. Date: Jun. 26, 2014

(65) Prior Publication Data
US 2016/0001282 A1    Jan. 7, 2016

(30) Foreign Application Priority Data

Dec. 18, 2012  (DE) .......... 10 2012 112 498
Dec. 18, 2013  (DE) .......... 10 2013 114 336

(51) Int. Cl.
*B01L 3/02* (2006.01)
*A61M 5/315* (2006.01)

(52) U.S. Cl.
CPC ......... *B01L 3/0224* (2013.01); *A61M 5/3155* (2013.01); *A61M 5/31505* (2013.01); *B01L 3/0234* (2013.01); *B01L 2200/023* (2013.01); *B01L 2200/028* (2013.01); *B01L 2200/0684* (2013.01); *B01L 2300/06* (2013.01); *B01L 2400/0478* (2013.01)

(58) Field of Classification Search
CPC .... B01L 3/0217; B01L 3/0206; B01L 3/0224; B01L 3/0234; B01L 3/022; G01F 11/06; B05B 11/025; B05B 11/3005; B05B 11/3007; B05B 11/3008
See application file for complete search history.

(56) References Cited

U.S. PATENT DOCUMENTS

| | | | | |
|---|---|---|---|---|
| 2,648,334 A | * | 8/1953 | Brown | A61M 5/24 604/205 |
| 4,526,294 A | * | 7/1985 | Hirschmann | B01L 3/0282 222/309 |
| 4,750,373 A | * | 6/1988 | Shapiro | B01L 3/0234 422/513 |
| 5,284,132 A | * | 2/1994 | Geier | A61M 11/02 128/200.22 |

(Continued)

FOREIGN PATENT DOCUMENTS

| | | |
|---|---|---|
| CA | 2679675 A1 | 9/2008 |
| CN | 101663096 | 3/2010 |

(Continued)

*Primary Examiner* — Brian R Gordon
(74) *Attorney, Agent, or Firm* — Verrill Dana, LLP; John W. Powell

(57) ABSTRACT

A dosing pipette for discharging a medium, wherein the pipette has a housing and a dosing piston. The housing has a dosing geometry which can be decoupled from the housing.

9 Claims, 13 Drawing Sheets

(56) References Cited

U.S. PATENT DOCUMENTS

| | | | |
|---|---|---|---|
| 6,322,542 B1* | 11/2001 | Nilson | A61M 31/00 604/257 |
| 7,798,185 B2* | 9/2010 | Py | A45D 34/04 141/329 |
| 9,770,559 B2* | 9/2017 | Armstrong | A61M 5/31526 |
| 2004/0162528 A1 | 8/2004 | Horvath et al. | |
| 2012/0283653 A1 | 11/2012 | MacDonald et al. | |
| 2012/0283657 A1 | 11/2012 | Kouyoumjian et al. | |

FOREIGN PATENT DOCUMENTS

| | | |
|---|---|---|
| DE | 3604826 | 10/1986 |
| WO | 2000/018453 | 4/2000 |
| WO | 2004/054720 | 7/2004 |

\* cited by examiner

DOSING PIPETTE

CROSS REFERENCE TO RELATED APPLICATIONS

This application is a National Stage of International Application No. PCT/EP2013/077210 filed on Dec. 18, 2013, which claims priority to German Application No. 102012112498.1 filed on Dec. 18, 2012 and German Application No. 102013114336.9 filed on Dec. 18, 2013, the contents of which are hereby incorporated by reference in their entirety.

TECHNICAL FIELD

The invention relates to a dosing pipette for discharging a medium according to the preamble of claim 1.

BACKGROUND ART

From the background art, several pipettes and sampling systems for different media, especially for fluid media, are known. These find application not only in many instances of daily life but also in industrial applications for extracting fluids or other media from a container.

Particularly often the known pipette systems find application in the field of medicine. In these pipette systems the liquid medium is most often drawn into the pipette system by means of a hand-operated piston. In this regard, the operator must orient him/herself to the scaling on the pipette receptacle. In other words, the user can freely move the suction piston of the pipette system within the dosing scale.

Thereby, it is often the case that an over- or under-dosing occurs because the operator draws the suction piston above or below the desired scale as a result of reading errors or reading inaccuracies.

This furthermore means that the dosing is not reproducible because variations can arise with each uptake. Particularly in the medical field, an over- or under-dosing can have negative repercussions. An over-dosing can, for example, be damaging to health, whereas an under-dosing can delay the healing process.

A further disadvantage of pipette systems from the background art is that, during intake of the medium, air bubbles often arise within the area of the dosing volume in the pipette system. These air bubbles can result in the drawn-in amount of the medium not corresponding to the amount on the dosing scale. Furthermore, air inclusions particularly in the medical field can be life-threatening for patients.

A dosing device for drawing-in and discharging of a flowable medium is, for example, known from WO 2004/054720. This dosing device comprises an inlet and an outlet which are arranged separately from one another. A dosing and expulsion chamber is therefore provided between the inlet and the outlet. However, the dosing device is a permanent component of the container from which the medium is extracted and cannot be handled separately from that container.

A further dosing device is known from WO 00/18453. In this case, the desired amount can be adjusted by means of a wheel which is located on a container closure. However, this dosing device is also only able to be used in combination with an associated container.

OBJECT OF THE INVENTION

It is the object of the invention to enable a dosed extraction of a medium, especially a fluid medium, from a container. In particular, it is an object of the invention, to provide a pipette system with which a specific dosing volume can be set and with which the dosing volume is reproducible.

Furthermore, it is an object of the invention to provide a pipette system with which an air-free and bubble-free suction or intake of the medium is possible. It is also an object of the invention to make a system available with which a broad spectrum of customer requirements with respect to the dosing volume can be covered with substantial component uniformity.

Furthermore, a pipette system should be provided which is easily disassembled and easily cleaned. In addition, the pipette system should be constructed such that it can also be used by untrained, for example, older people.

Solution of the Object

In a typical embodiment, a dosing pipette for delivering a medium, especially a liquid medium, includes a dosing piston and a housing. The housing contains a dosing geometry, wherein the dosing geometry can be decoupled from the housing in the dosing pipette according to the invention.

In a typical embodiment, the dosing piston of the dosing pipette is constructed of multiple parts and is comprised of a piston and a dosing insert. A unitary construction of the dosing piston is also possible. Furthermore, the dosing piston in a typical embodiment is removable and/or replaceable. In this way, the dosing piston can, on the one hand, be adapted to customer requirements and, on the other hand, be removed for cleaning.

In a typical embodiment, the piston of the dosing piston comprises at least one dosing channel. Preferably, the piston comprises a plurality of dosing channels which are distributed around the circumference and extend over at least a portion of the length of the piston. The length of the channels can be varied by means of the dosing insert, which is slid onto the piston as a kind of sleeve.

In order to provide various dosing paths, which in turn cater for various dosing volumes, the dosing insert comprises a dosing geometry. With respect to the dosing geometry, in a typical embodiment it is a matter of a stepped geometry which is configured such that the length of the dosing channels of the piston is limited to the desired lengths of the dosing paths. This furthermore results in that the dosing pipette is able to be manufactured in various embodiments with respect to the dosing volumes with substantial component uniformity merely through an exchange of the dosing insert.

In this way, for example, in one embodiment the dosing region of the dosing pipette of 1 ml to 6 ml can be subdivided into 1 ml measures, whereas the dosing region in another embodiment of 0.5 ml to 5 ml is subdivided into 0.5 ml measures. As illustrated by the examples, the dosing volumes of the dosing pipette and thereby the dosing of the medium to be delivered can be adjusted via the dosing insert.

Furthermore, the above-mentioned embodiments demonstrate that the housing of the dosing pipette is adapted for receiving different dosing pistons, wherein particularly the dosing insert of the dosing piston is differently configured.

In a typical embodiment, the dosing piston is essentially form-fittingly connected with the housing, because at least one stop reaches into the dosing channels and/or the dosing geometry of the dosing piston when the dosing pipette is assembled. The dosing piston can thereby nevertheless still be drawn out of the housing along the length of the adjusted dosing path and subsequently pushed back into it again. For defining the dosing paths, the dosing geometry comprises at least one dosing stop which is in operative connection with a rigid stop as a limiting means. In a typical embodiment, the dosing stop limits the length of the dosing path to the desired length and furthermore ensures that the dosing piston cannot be drawn further out of the housing than intended.

In an embodiment, the stop is integrated in a multi-part housing rim. A part of the housing rim is configured integral with the housing. The stop or the stops in a typical embodiment are configured unitary with a housing flange and preferably comprise the form of a lobe and/or a peg. The housing rim is closed by the housing flange in that the stops are inserted into recesses provided for them. This takes place after the dosing piston has been introduced into the housing.

In order to ensure a reliable closure of the housing rim, the recesses for receiving the stops are located in the region of the largest diameter of the housing, which corresponds to a tangential point, or are attached to the housing such that the stops of the housing flange have to be pushed over the tangential point in order to be inserted into the recesses.

In a typical embodiment, with the housing and the hosing rim it is indeed a matter of two parts, although to save costs these can be manufactured as one component, preferably as an injection molded part. In that case, the housing flange after the part fabrication is connected with the housing in the region of the stops, wherein a perforation in the connection area of the two parts ensures that the housing flange can be simply separated, particularly sheared-off, from the housing before it is connected to the housing. The housing flange with the stops can thus be configured such that a disassembly of the dosing pipette is prevented after the assembly.

In a further embodiment, the stop is integrated in a locking ring. The locking ring in a typical embodiment encompasses more than half of the circumference of the housing, preferably about ¾ of the circumference of the housing and is typically attached below the housing rim, which in this case is preferably configured in one piece.

With below the housing rim a position is thus described which means that the locking ring is located on a proximal side of the housing rim. By the proximal side, the side is thereby described which is directed towards the center of the body and at which end of the housing a discharge opening is located through which a medium can be drawn into the dosing pipette via the dosing piston and discharged again.

The locking ring can in a typical embodiment of the dosing pipette be pushed down, whereby a removal of the dosing piston becomes possible. In this way, it is possible that the individual parts of the dosing pipette can be cleaned. Thereafter, by inserting the dosing piston into the housing and subsequently sliding on the locking ring, the dosing pipette can be assembled again and used anew.

The stop and the dosing piston in a typical embodiment are configured such that the dosing piston is mounted at least partially rotatable in the housing. Preferably, a twisting of the dosing piston is only possible in an empty condition of the dosing pipette. Through the possibility of a rotation of the dosing piston, different reproducible dosing volumes can be set with the dosing pipette.

To this end, in a typical embodiment the housing rim comprises markings on a distal side, whereby with distal a side directed away from the center of the body in the use position is described. Furthermore, the piston comprises a projection on the distal side, which may for example be configured as an arrow-head geometry. By twisting the dosing piston in the housing, depending on the position set via the twisting, the projection points to a marking on the housing rim. Through this indication it becomes clear to the user which dosing volume is set. Furthermore, the possibility exists that user information is attached on the distal side of the piston flange. This may be printed on or stamped or be introduced as recess and/or embossing already in the part fabrication, for example during injection molding.

In order to prevent an unwanted displacement of the dosing insert on the piston of the dosing piston, the dosing insert comprises a protrusion on the proximal side which is configured complementary to a retaining element which is located in the region of the proximal end of the piston. The protrusion and the associated retaining element may comprise many different shapes. In a typical embodiment, the protrusions are configured as rounded or ellipsoid-shaped elevations.

The protrusions in the dosing insert are preferably located in an opening which is located in a sort of base on a proximal side of the dosing insert. The recess is in a typical embodiment configured complementary to the region of the piston in which the retaining elements are located. In this way, a form-fitting connection arises between the piston and the dosing insert which prevents an unwanted displacement of the dosing insert on the piston.

Furthermore, the dosing piston comprises a piston lip and a sealing pin. In a typical embodiment the piston lip is formed in one piece with the dosing insert of the dosing piston, whereas the sealing pin is formed in one piece with the piston.

The sealing pin ensures that a clean application is possible and closes up the discharge opening in the housing in an empty state, is therefore in a typical embodiment configured complementary to the discharge opening. In a typical embodiment the discharge opening in the housing is configured as a cylindrical and/or a conical hollow.

The piston lip ensures that an air- and bubble-free suction/intake and/or emptying of the dosing pipette is facilitated. Furthermore, this configuration ensures that only a very minor residual-/dead-volume is present in the emptied state of the dosing pipette.

DESCRIPTION OF THE DRAWINGS

Further advantages, features and details of the invention are apparent from the following description of preferred embodiments as well as with reference to the drawings; which show in FIG. 1 a cross-sectional view longitudinally through a first dosing pipette according to the invention in an emptied use position.

EMBODIMENT

Figure 1:
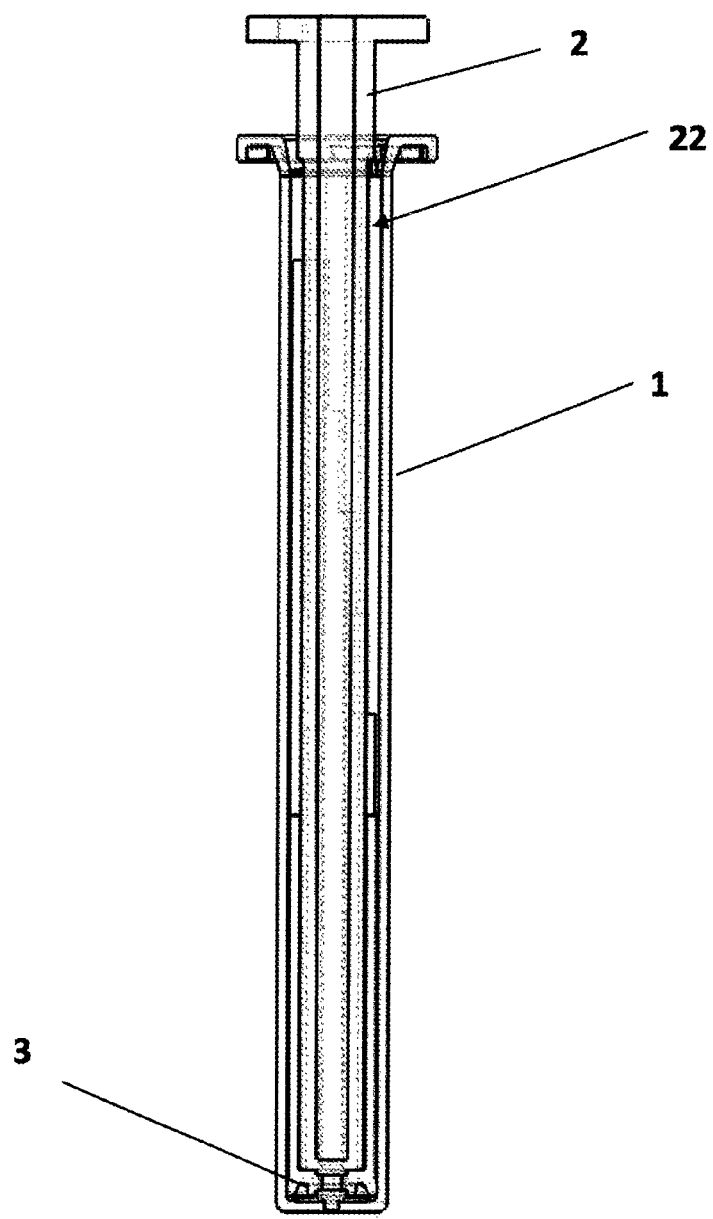

In FIG. 1 a cross-sectional view longitudinally through a typical embodiment of a dosing pipette according to the invention is illustrated, which is configured for outputting and/or for intake of a medium.

A cross-sectional plane with longitudinal through the system is thus described which extends from a proximal end of the dosing pipette to a distal end of the dosing pipette. With the proximal end, an end of the dosing pipette directed towards a body is described in which a discharge opening 11 is located. With the distal end, an end of the dosing pipette directed away from the body is described which is located at the opposite side from the end with the discharge opening 11.

In a typical embodiment the dosing pipette is comprised of a housing 1 and a dosing piston 22. The dosing piston 22 in a typical embodiment is comprised of a piston 2 and a dosing insert 3.

Figure 2:
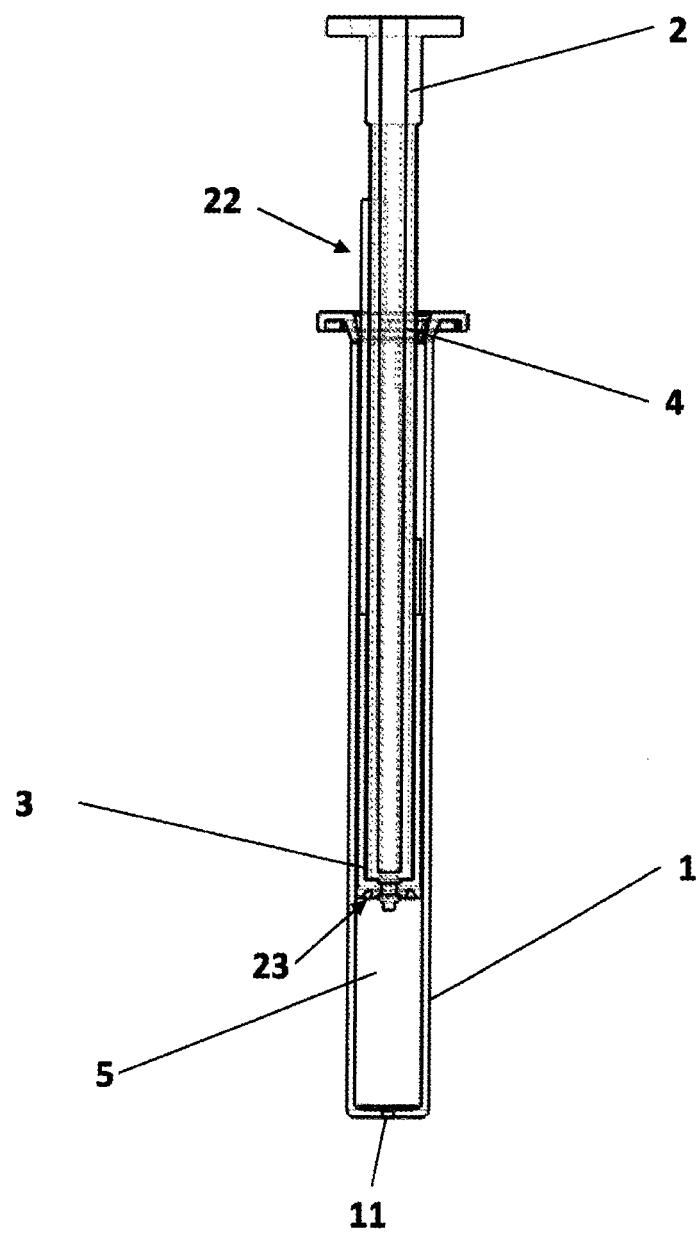
FIG. 2 a cross-sectional view longitudinally through the dosing pipette according to FIG. 1 in a drawn up use position.

In FIG. 2 the dosing pipette according to FIG. 1 is illustrated in a drawn out state. Through the drawing out of the dosing piston 22, a dosing volume 5 is generated in the housing 1 between the proximal end of the housing in the region of the discharge opening 11 and a proximal end 23 of the dosing piston 22. The dosing piston 22 can be maximally drawn out of the housing 1 up to a stop 4. The dosing volume 5 is thereby defined through an interaction of the dosing piston 22 and the fixed stop 4.

Figure 3:
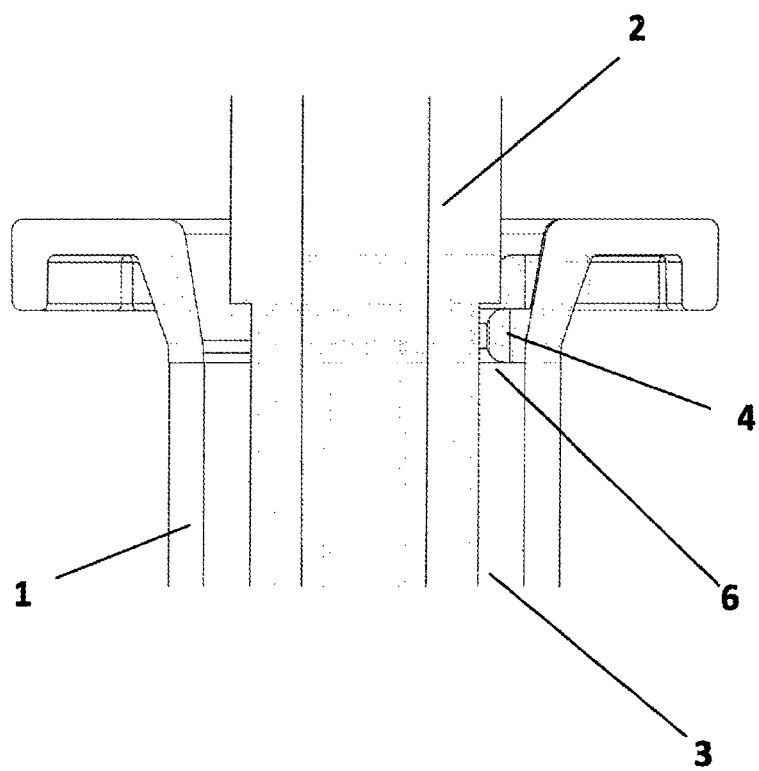
FIG. 3 a detail view of a region of the dosing pipette in which a stop is located.

In FIG. 3 a cross-sectional view is shown, which illustrates the region of the dosing pipette in which the rigid stop 4 is located. The dosing piston 22, which is comprised of the piston 2 and the dosing insert 3, can be drawn out of the housing 1 for as long until a dosing stop 6 strikes upon the fixed stop 4 and prevents a further withdrawal of the dosing piston 22. The dosing stop 6 and the stop 4 thereby come into operative connection and limit the withdrawal of the dosing piston 22.

Figure 4:
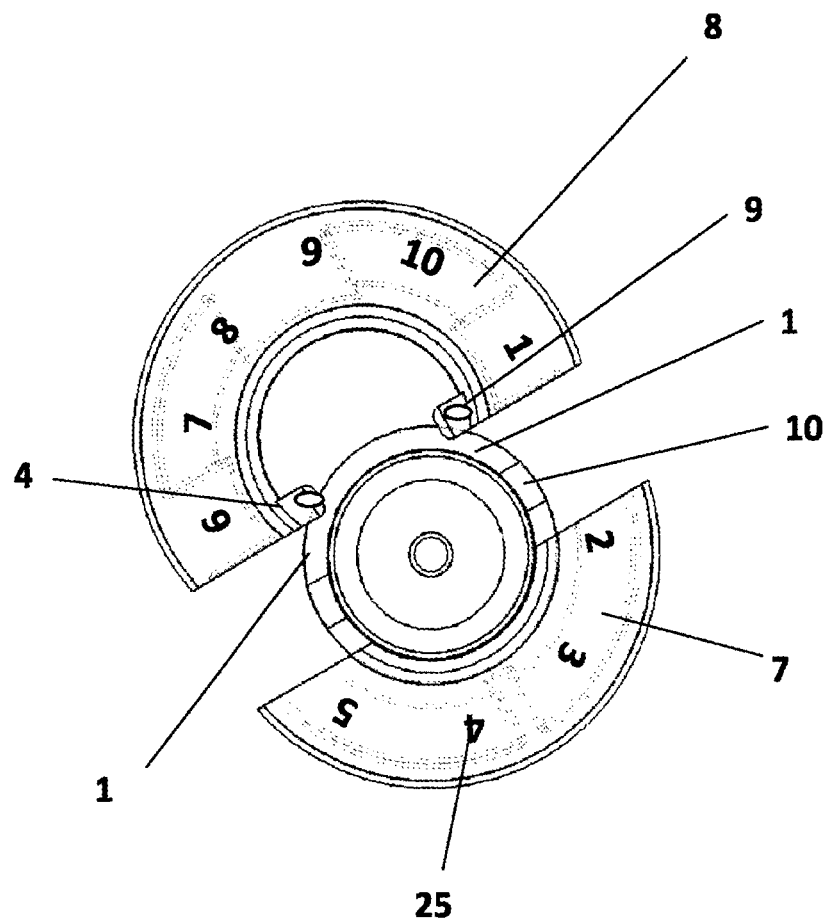
FIG. 4 a top view of a distal side of a housing with a multi-part housing rim.

In FIG. 4 a top view of a housing 1 is illustrated from a distal side. A housing rim 7 of the housing 1 is configured in two parts in the illustrated embodiment. A part of the housing rim 7 is integrally formed with the housing 1. The housing rim 7 furthermore includes a housing flange 8, which in turn is integrally formed with the fixed stops 4. The housing flange 8 with the fixed stops 4 is fabricated in a typical embodiment unitarily with the housing 1, for example as an injection molded part.

For the receipt of the stops 4, the housing 1 comprises at least one recess 10. In a one-piece construction of the housing 1 and the housing flange 8, these parts comprise a perforation 9 in the area of the stops 4 which enable a simple severing of the housing flange 8 from the housing 1. In an embodiment, the stops 4 are configured in the form of a lobe or a peg.

In a further embodiment the housing flange 8 is manufactured as a separate injection molded part. Advantageously, the housing flange 8 is manufactured in one-piece with the housing 1 as an injection molded part, whereby the production costs for the entire housing 1 are able to be reduced. Upon assembly of the dosing pipette, after the dosing piston 22 is inserted into the housing 1, the housing flange 8 with the stops 4 are pressed into the hollows 10 in the housing 1. The dosing piston 22 is thereby secured by the fixed stops 4 against withdrawal from the housing 1.

Figure 5:
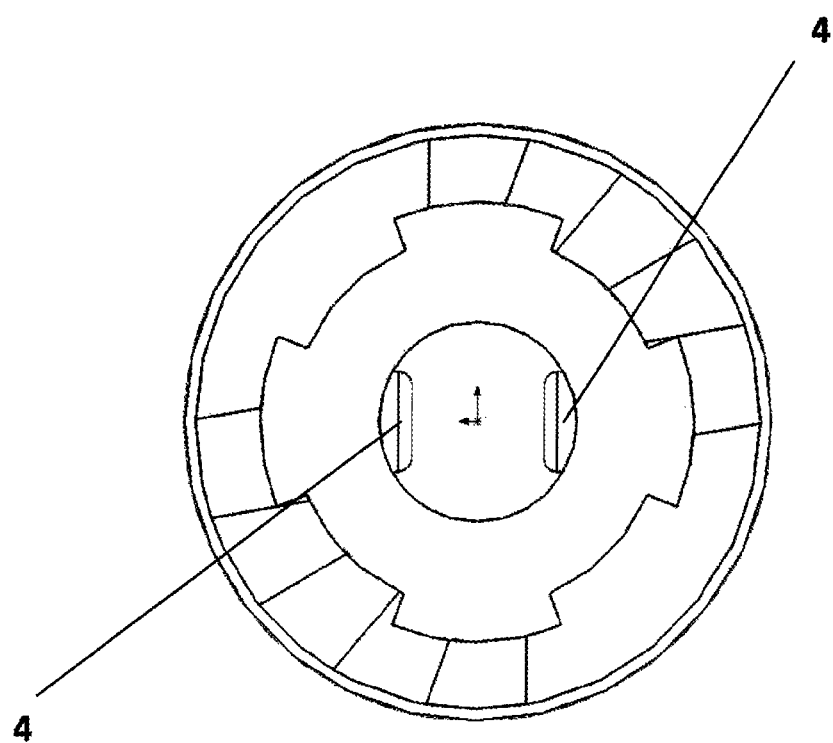
FIG. 5 a cross-sectional view transversely through the first housing above the stop.

In FIG. 5 a cross-sectional view through the housing rim 7 of the assembled housing 1 is illustrated with the stops 4 latched within the recesses 10. With the reference to a cross-sectional view transversely through the housing rim 7, a cross-sectional plane is described that is orthogonal to the longitudinal plane of FIG. 1.

By the engagement of the rigid stops 4 in the recesses 10 of the housing 1, an interlocking of the system takes place. By virtue of this system locking, it can be prevented that the dosing piston 22 is completely drawn out of the housing 1. In order to obtain a highly secure system locking, the recesses 10 are preferably located in the region of the largest diameter of the housing 1. This clamping effect can be reinforced when the recesses 10 are located away from the largest diameter of the housing 1 and the rigid stops on the housing flange 8 have to be pushed over the largest diameter in order to latch within the recesses 10.

In an embodiment, the housing flange 8 can be removed again after assembly, whereby it is facilitated that the dosing piston 22 can be removed and/or can be replaced.

Figure 6:
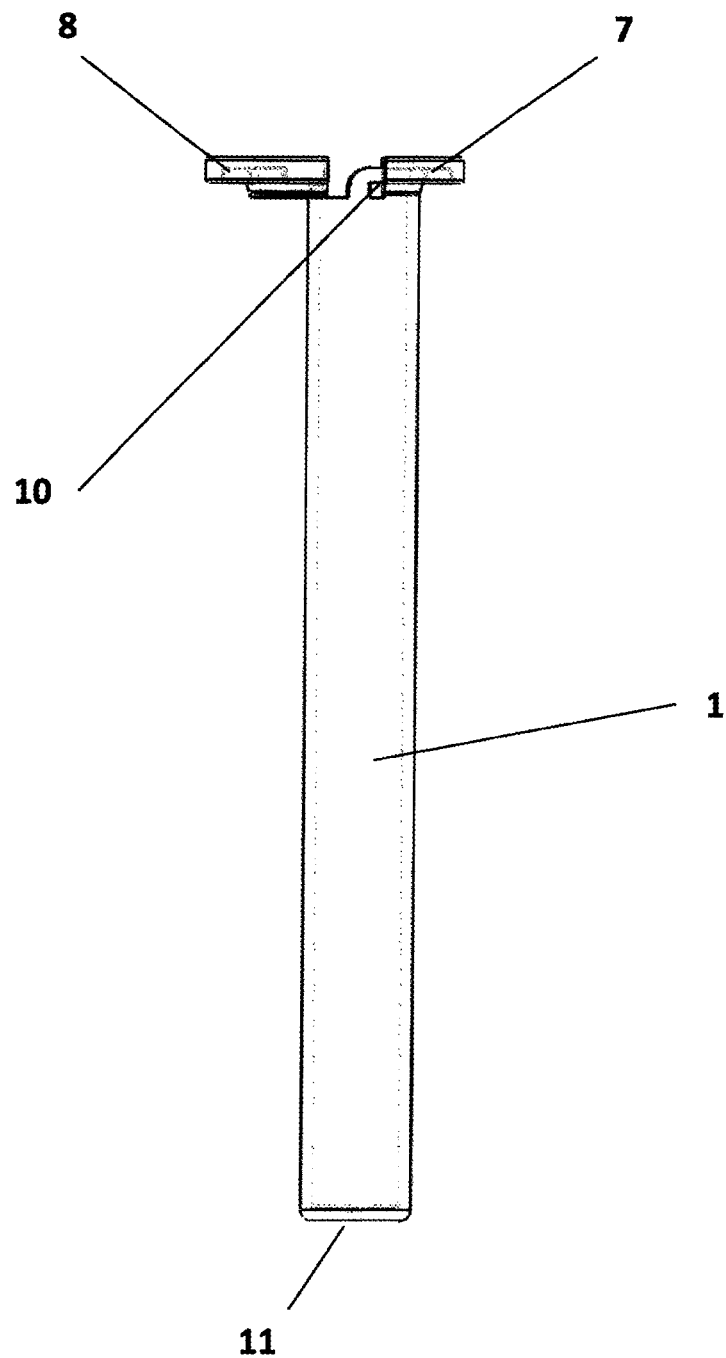
FIG. 6 a side view of a housing according to FIG. 4.

In FIG. 6 the fabrication part of the housing 1 and the housing flange 8 is illustrated, how it may for example be fabricated as an injection molded part. At the distal end of the housing a recess 10 can be seen, which is provided for receiving the rigid stops 4. By pressing the housing flange 8 onto the housing 1, the multi-part housing rim 7 is closed, as already described previously.

Furthermore, on the proximal side of the housing the discharge opening 11 is illustrated schematically. The discharge opening 11 in a typical embodiment is formed as a cylindrical or conical aperture and/or bore.

Figure 7A:
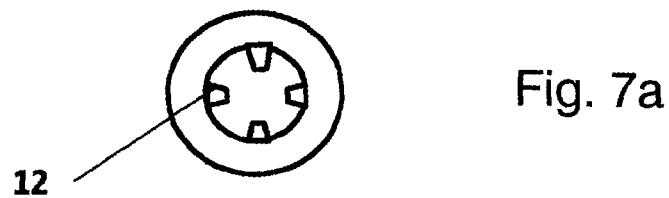
FIG. 7a-7c different views of a piston.
Figure 7B:
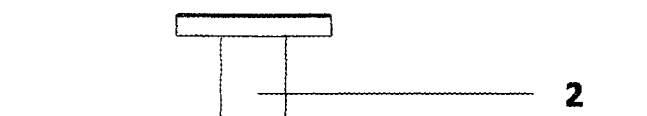
Figure 7C:
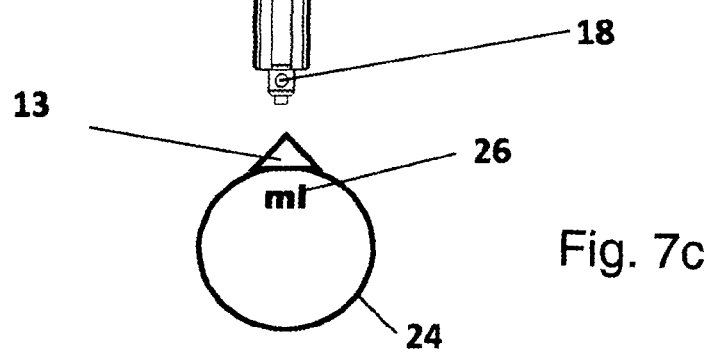

In the FIGS. 7a to 7c different views of the piston 2 of the dosing piston 22 are illustrated. In FIG. 7b a side view of the piston 2 is thereby illustrated. The piston 2 comprises at least one, preferably multiple dosing channels 12, which in a typical embodiment are distributed around and set into the periphery of the piston 2.

FIG. 7a shows a view from a proximal side of the piston 2 having the dosing channels 12. In FIG. 7c a view of the piston 2 from the distal side is illustrated.

On the distal side, the piston comprises a projection 13 on a piston flange 24 in order to enable and/or to facilitate the user in the setting of the dosing volume 5 in connection with the markings 25 on the housing rim 7 (see FIG. 4).

Furthermore, the projection 13 on the piston flange 24 results in that the dosing piston 22 can be more easily twisted in the housing 1 to the desired position. In order to enable this, the dosing piston 22 is supported at least partially rotatable in the housing 1 of the dosing pipette. Furthermore, the user information 26 can be applied to the upper side of the piston flange 24.

The piston 2 comprises on its proximal end a sealing pin 21, which is preferably formed complementary to the discharge opening 11 of the housing 1. Furthermore, the piston 2 comprises a retaining element 18 in the region of the proximal end. The retaining element 18 is thereby formed complementary to a protrusion 19 of the dosing insert 3.

Figures 8A, 8B:
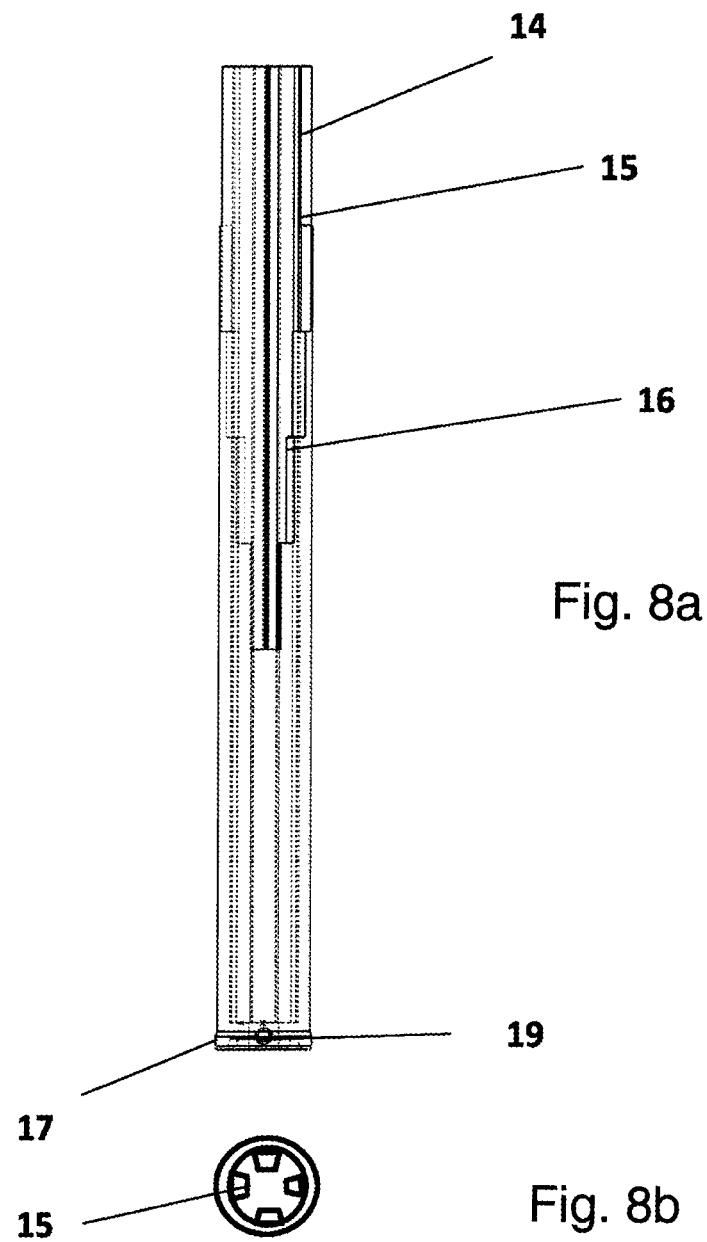
FIG. 8a-8b different views of a dosing sleeve.

An embodiment of the dosing insert 3 is illustrated in the FIGS. 8a and 8b. After the assembly with the piston 2, at least one dosing path 14, preferably multiple dosing paths 14, are determined via the dosing insert 3. The dosing path 14 thereby extends between the fixed stop 4 and a step-shaped abutment surface 15, which comprise a plurality of dosing stops 6 and corresponds to a dosing geometry 16. In this way the precise dosing volume 5 can be determined by the length of the dosing path 14.

In a typical embodiment, the dosing insert 3 comprises a dosing geometry 16 in order to enable many different dosing paths 14. For this, the dosing geometry 16 is preferably introduced over the circumference in the dosing insert 3. The dosing insert 3 is thereby so formed that, after it is placed on the piston, it limits the dosing channels 12 to the length of the dosing paths 14.

In order to obtain a form-fitting connection between the piston 2 and the dosing insert 3, the piston 2 comprises the retaining element 18 and the dosing insert 3 the protrusion 19 at their proximal ends. By applying a dosing insert 3 which has another dosing geometry 16, different dosing pipettes, with which many different dosing volumes 5 can be achieved, can be created with the same piston 2 and the same housing 1. Accordingly, the housing 1 is adapted to receive different dosing pistons 22, wherein particularly the dosing insert 3 is differently configured. Therefore, a precise dosing, especially a precise and reproducible dosing volume 5, is settable via the dosing insert.

Figure 9:
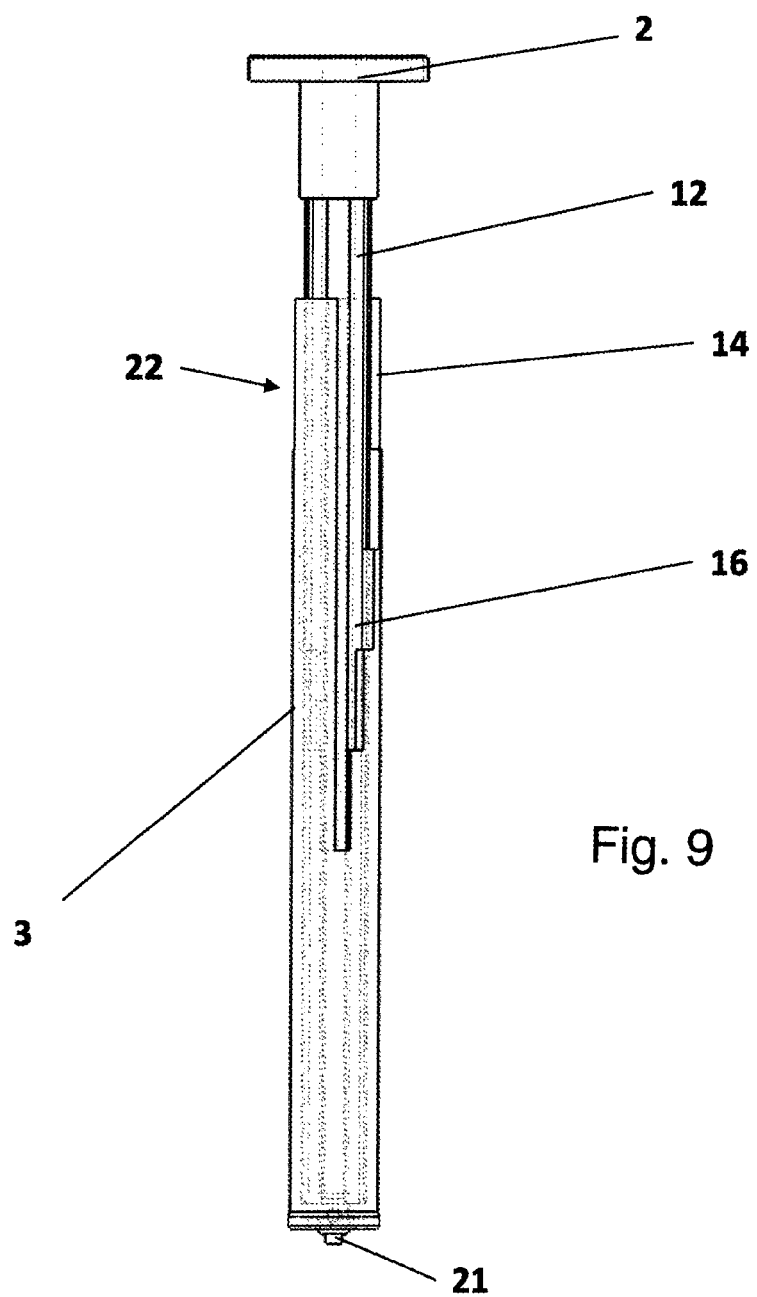
FIG. 9 a side view of an assembled dosing piston.

In FIG. 9 the dosing piston 22 of piston 2 and dosing insert 3 is illustrated in the assembled state. Thereby is clearly to be seen that the length of the dosing channels 12 is confined to the length of the dosing paths 14 via the dosing geometry 16.

Figure 10:
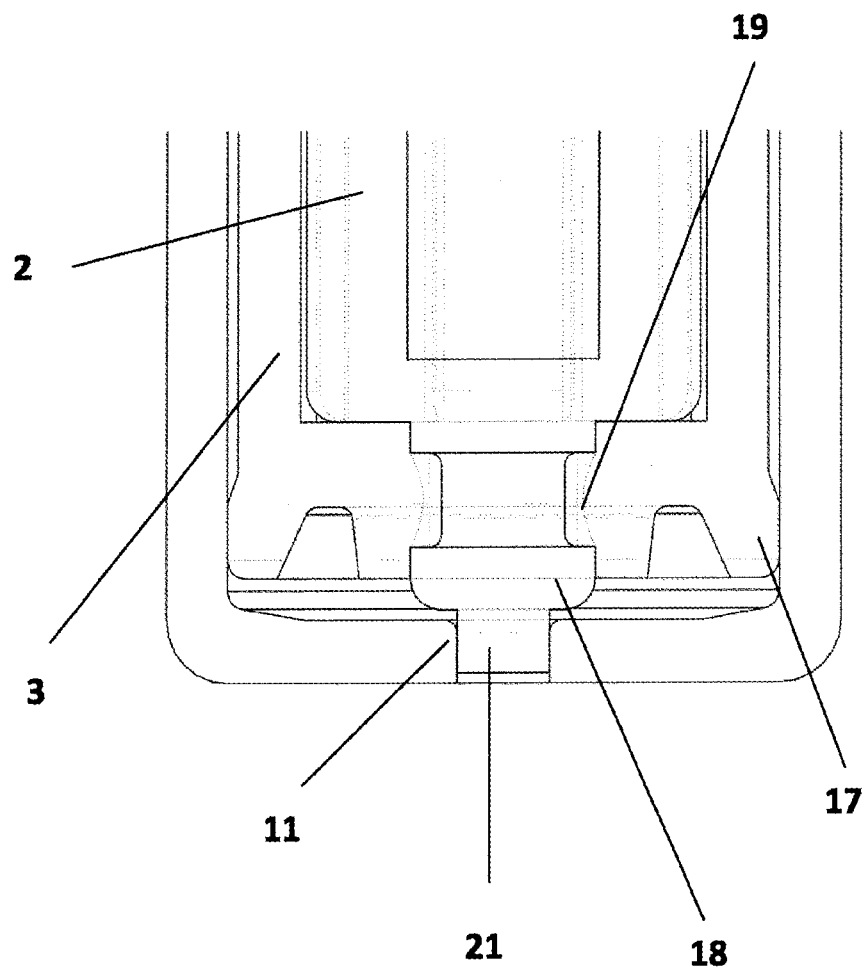
FIG. 10 a detailed cross-sectional view of a proximal end of the dosing pipette.

In FIG. 10 a detailed cross-sectional view through the proximal end of the dosing pipette is illustrated. Because the retaining element 18 of the piston 2 receives the protrusion 19 of the dosing insert 3, a form-fitting connection arises which in the assembled state of the dosing pipette is non-detachable.

Furthermore is illustrated that the sealing pin 21 closes and/or seals the preferably cylindrical or conical discharge opening 11 of the housing. In this way, for example, a clean application of a medicament is possible. Furthermore is apparent that in the emptied state of the dosing pipette almost no residual volume or dead volume in the interior of the dosing pipette is present. A piston lip 17 of the dosing insert 3 ensures that an air-free and bubble-free intake and discharge of the medium is facilitated via the dosing pipette.

Figure 11:
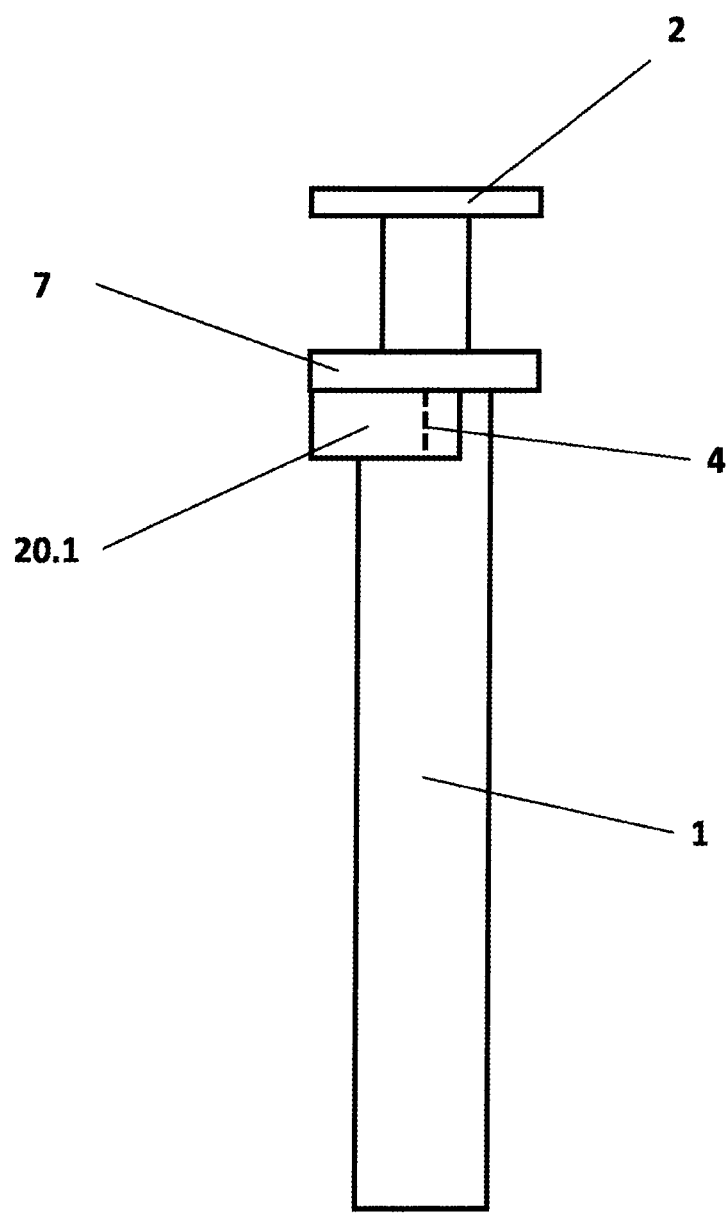
FIG. 11 a further embodiment of a dosing pipette according to the invention.

In FIG. 11 a further typical embodiment of a dosing pipette according to the invention is illustrated. This comprises a continuous and non-separated housing rim 7. Below the housing rim 7 in this embodiment a locking ring 20 is provided.

Because the locking ring 20 only encompasses a portion of the housing 1, it can be removed from the housing 1, whereby the dosing piston can then be drawn out of the housing 1. Thus, the dosing piston 22 and the housing 1 can be cleaned and/or sterilized.

Figure 12:
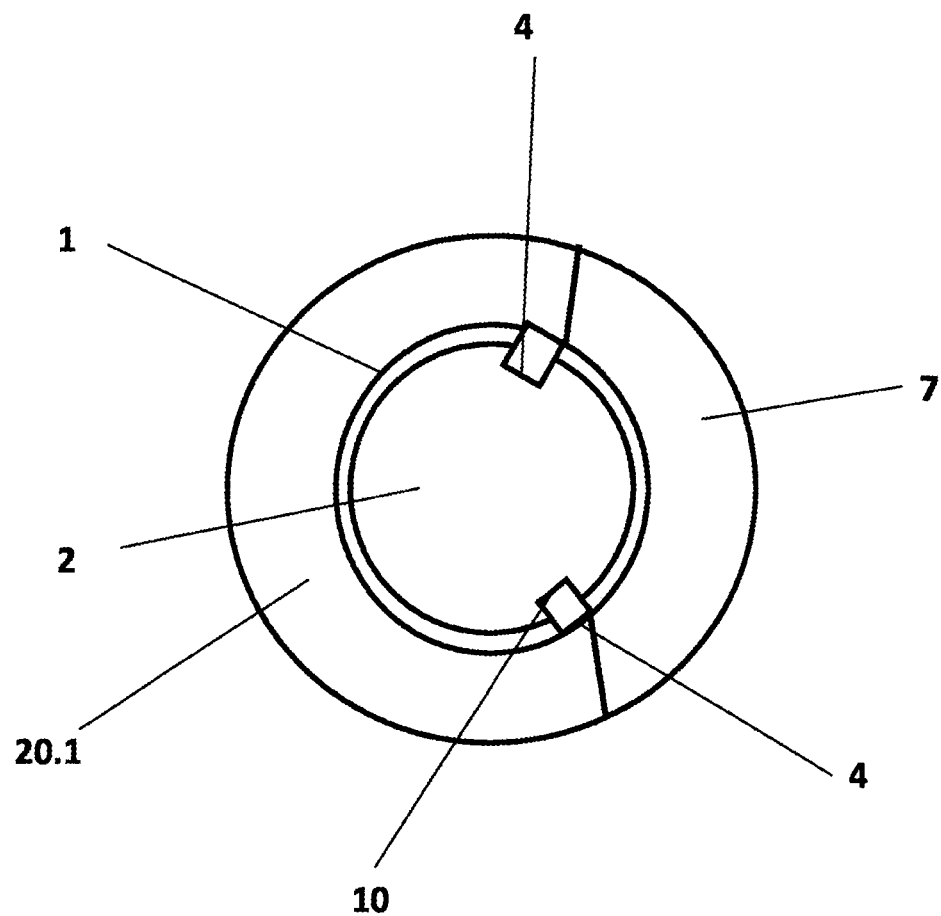
FIG. 12 a cross-section through the dosing pipette of FIG. 11 having a first embodiment of the locking ring.
Figure 13:
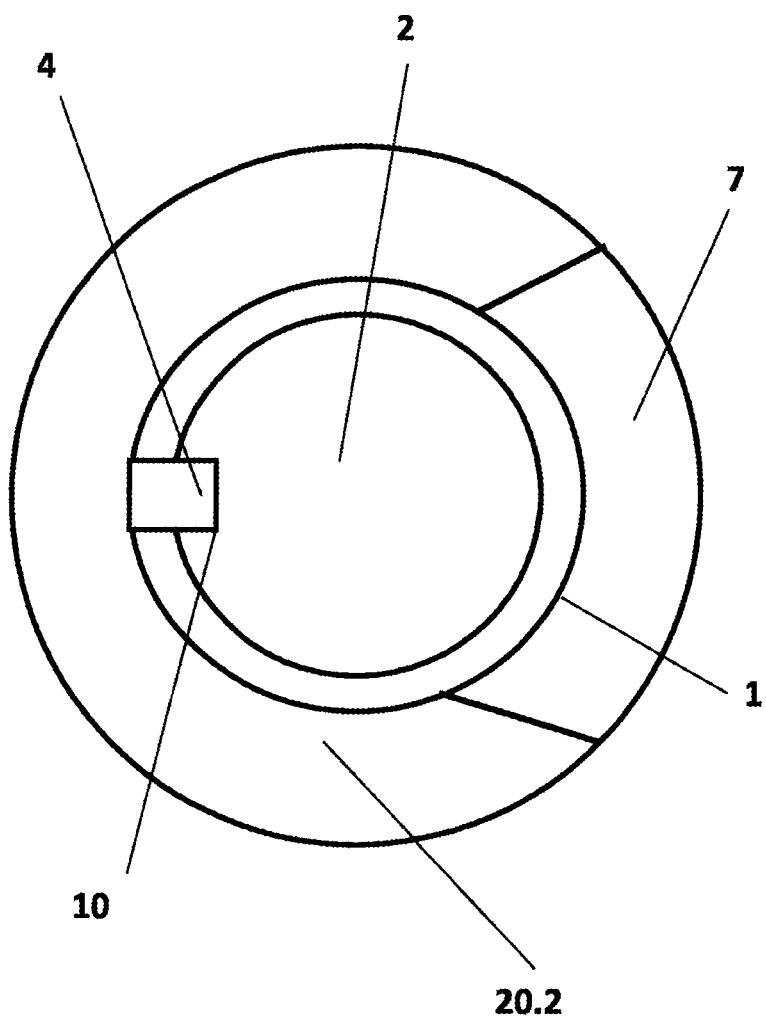
FIG. 13 a cross-section through the dosing pipette of FIG. 11 having a further embodiment of the locking ring.

The locking ring 20 in a typical embodiment encloses about ¾ of the housing circumference of the housing 1. In FIGS. 12 and 13 two different embodiments of the locking ring 20 are illustrated. Whereas in FIG. 12 a locking ring 20 with two fixed stops 4 is illustrated, FIG. 13 shows a locking ring 20 with one fixed stop 4.

By virtue that the locking ring 20 encompasses more than half of the housing circumference of the housing 1, it is prevented that it can easily be pushed off the housing.

For cleaning the dosing pipette, the locking ring 20 is taken off the housing 1 and thereafter the dosing piston 22 is removed. After the cleaning, the dosing piston 22 can be inserted into the housing 1 again and thereafter the locking ring 20 is pressed onto the housing, whereby the fixed stops 4 must latch into the recess 10 of the housing 1.

In a further, non-illustrated embodiment, the fixed stop 4 is configured hemi-spherically shaped or as a cone. In this embodiment the locking ring need not be removed in order to remove the dosing piston 22. For removal of the dosing piston 22 it is drawn with high pulling force over the hemi-spherically shaped or cone shaped stop 4.

This is possible because the stop 4 in this embodiment is at least partially movable due to the resilience of the locking ring. After the cleaning, the dosing piston 22 can be inserted over the stop 4 into the housing 1 again. For this, a higher force exertion is again necessary.

REFERENCE SIGN LIST

1 housing
2 piston
3 dosing insert
4 stop
5 dosing volume
6 dosing stop
7 housing rim
8 housing flange
9 perforated connection
10 recess
11 discharge opening
12 dosing channel
13 projection
14 dosing path
15 abutment surface
16 dosing geometry
17 piston lip
18 retaining element
19 protrusion
20 locking ring
21 sealing pin
22 dosing piston
23 proximal side
24 piston flange
25 marking
26 user information

The invention claimed is:

1. A dosing pipette for discharging a medium, wherein the dosing pipette comprises:
   a housing for receiving the medium,
   a dosing piston assembly that is movable within the housing, and
   a fixed stop that is provided on the housing,
   wherein the housing is elongate and extends from a proximal end of the housing having a first opening to a distal end of the housing having a second opening through which the dosing piston assembly is at least partially inserted into the housing,
   wherein the dosing piston assembly comprises a piston and a dosing insert, wherein the piston and the dosing insert are detachable from each other;
   wherein the dosing insert is arranged coaxially with the piston and is surrounding the piston,
   wherein the dosing insert comprises a step-shaped abutment surface with a plurality of steps extending around a circumferential direction of the dosing insert,
   wherein each step is a dosing stop configured to limit movement of the dosing piston assembly within the housing in an axial direction of the housing away from the proximal end of the housing by abutment with the fixed stop, and
   wherein the dosing piston assembly is configured and arranged to be at least partially rotatable in the housing.

2. The dosing pipette according to claim 1, wherein the dosing piston assembly can be separated from the housing and can be replaced by another dosing piston assembly.

3. The dosing pipette according to claim 1, wherein an outer surface of the dosing piston assembly is adapted to contact an inner surface of the housing.

4. The dosing pipette according to claim 1, wherein the housing comprises a housing rim or a locking ring, and wherein the fixed stop is integrally formed with the housing rim or with the locking ring, respectively.

5. The dosing pipette according to claim 1, wherein the piston comprises a retaining element, and wherein the dosing insert comprises a protrusion which is connected to the retaining element to provide a form-fitting connection between the dosing insert and the piston.

6. The dosing pipette according to claim 1, wherein the dosing piston assembly comprises a piston lip engaged with an inner surface of the housing in a for form-fitting manner.

7. The dosing pipette according to claim 1, wherein the dosing piston assembly comprises a sealing pin which is formed complementary to the first opening of the housing.

8. The dosing pipette according to claim 1, wherein the piston comprises a dosing channel, and wherein the fixed stop extends into the dosing channel.

9. The dosing pipette according to claim 1, wherein the housing comprises a recess, and wherein the fixed stop latches into the recess.

* * * * *